(12) United States Patent
Moss

(10) Patent No.: US 6,533,743 B1
(45) Date of Patent: Mar. 18, 2003

(54) ANGULARLY ADJUSTABLE TRACTION APPARATUS

(76) Inventor: John S. Moss, 1400 Washington Ave., Fredericksburg, VA (US) 22401

( * ) Notice: Subject to any disclaimer, the term of this patent is extended or adjusted under 35 U.S.C. 154(b) by 0 days.

(21) Appl. No.: 09/679,770

(22) Filed: Oct. 5, 2000

(51) Int. Cl.[7] .................................................. A61F 5/00
(52) U.S. Cl. ............................ 602/32; 602/33; 602/36; 606/241
(58) Field of Search .................... 602/32–33, 35–36, 602/38–40; 606/240–242, 243–244; 128/845, 878, 879

(56) References Cited

U.S. PATENT DOCUMENTS

| | | | |
|---|---|---|---|
| 4,653,482 A | * | 3/1987 | Kurland ........................... 5/601 |
| 5,020,525 A | * | 6/1991 | Ewing et al. .................. 602/27 |
| 5,290,220 A | * | 3/1994 | Guhl ........................... 128/882 |
| 5,865,780 A | | 2/1999 | Tuite |
| 5,875,781 A | * | 3/1999 | Klaus ........................... 128/869 |
| 5,961,512 A | * | 10/1999 | Purnell ........................... 606/1 |

* cited by examiner

*Primary Examiner*—Denton D. DeMille
*Assistant Examiner*—Quang D Thanh
(74) *Attorney, Agent, or Firm*—Henderson & Sturm LLP

(57) ABSTRACT

An angularly adjustable traction apparatus (10) for applying traction forces to a patient's limb wherein the apparatus (10) includes a base platform member (20) provided with a rail unit (14) that is raised relative to the base platform member (20) and a limb immobilizing unit (12) and pulley unit (13) slidably disposed on the rail unit (14) and adapted to be angularly adjusted relative thereto; wherein, the pulley unit (13) includes a support post member (50) and a pulley member (60) suspended from the support post member (50) and provided with a bracket element (61) whose height can be varied to the base platform member (20).

7 Claims, 3 Drawing Sheets

ANGULARLY ADJUSTABLE TRACTION APPARATUS

BACKGROUND OF THE INVENTION

1. Field of the Invention

The present invention relates to the field of traction apparatus in general and in particular to a traction apparatus having angularly and laterally adjustable structural components to accommodate individual patents and/or medical procedures.

2. Description of Related Art

As can be seen by reference to the following U.S. Pat. Nos. 5,074,291; 3,850,166; 5,441,480; 5,961,512 and 5,632,726, the prior art is replete with myriad and diverse arrangements for immobilizing and/or placing a patient's limbs in a traction mode.

While all of the aforementioned prior art constructions are more than adequate for the basic purpose and function for which they have been specifically designed, they are uniformly deficient with respect to their failure to provide a simple, efficient, and practical apparatus for applying traction to a patient's limbs while the patient reclines in a supine position and wherein the apparatus employs both laterally and angularly adjustable components to accommodate the needs of individual patients.

As most physicians are well aware, the proper application of traction forces is a necessary requirement when setting bone fractures and performing other related medical procedures.

As a consequence of the foregoing situation, there has existed a longstanding need in the medical field for a new and improved angularly adjustable traction apparatus that can be employed in both the straight anterior and direct superior modes as well as positions intermediate thereof; and, the provision of such a device is a stated objective of the present invention.

BRIEF SUMMARY OF THE INVENTION

Briefly stated, the angularly adjustable traction apparatus that forms the basis of the invention comprises in general a main support unit, a limb immobilizing unit, a pulley unit, and a rail unit wherein the limb immobilizing and pulley units are angularly and laterally adjustable relative to the main support unit and the rail unit and the pulley unit is vertically adjustable as well.

As will be explained in greater detail further on in the specification, the main support unit comprises a base platform member that is dimensioned to fit under a patient's upper torso in both versions of the preferred embodiment of the invention.

In addition, in one version of the preferred embodiment the limb immobilizing unit includes the first rigid support post member surrounded by a hollow padded member and in the second version of the preferred embodiment, the limb immobilizing unit includes the first rigid support post member; however, in this instance the padded member has a generally C-shaped configuration and is laterally offset from the first support post member such that the padded member can be rotated from an anterior to a superior position relative to a patient's limb.

Furthermore, in both the first and second versions of the preferred embodiment, the pulley unit comprises a pulley member suspended from a second support post member wherein on one version of the invention, the pulley member is suspended from an adjustable bracket element slidably received on the second support post member which is a solid one piece member; and, in the second version of the invention, the pulley member is suspended from a fixed bracket element that is secured to the top section of a telescoping second support post member.

As will also be explained further on in the specification, the rail unit is operatively attached to the base platform member and comprises an elongated rail member in one version of the preferred embodiment and a pair of widely spaced, contoured rail segments in the other version of the preferred embodiment; and, wherein in both versions of the preferred embodiment of the invention, the limb immobilizing unit and the pulley unit are laterally displaceable to one another and angularly adjustable relative to the rail unit via universal swivel joints and adjustment locking mechanisms.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
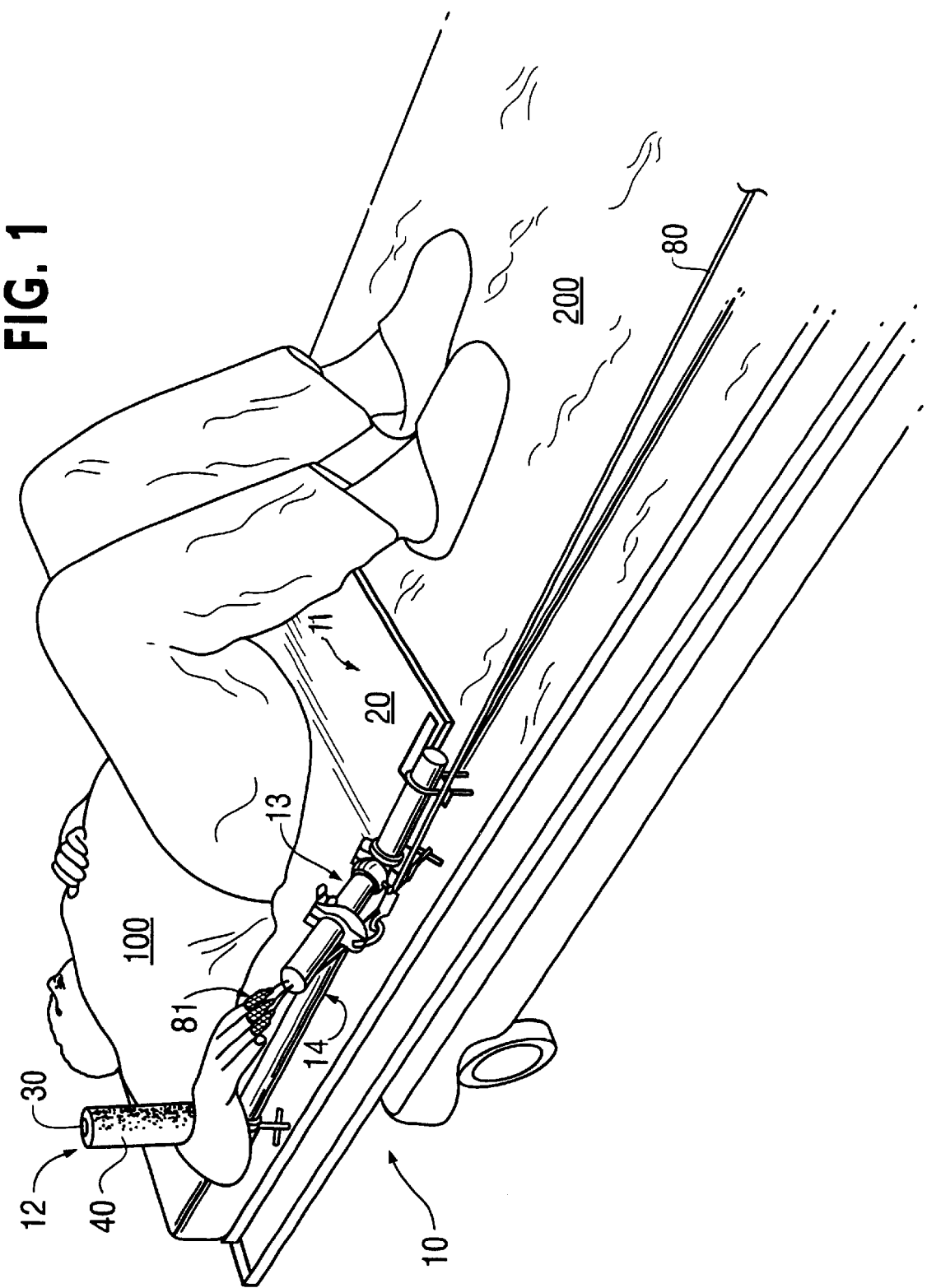
FIG. 1 is a perspective view of the first version of the adjustable angle traction apparatus that forms the basis of this invention in use.

As can be seen by reference to the drawings, and in particular to FIG. 1, the angularly adjustable traction apparatus that forms the basis of the present invention is designated generally by the reference number (10). The apparatus (10) comprises in general a main support unit (11), a limb immobilizing unit (12), a pulley unit (13) and a rail unit (14). These units will now be described in seriatim fashion.

Figure 2:
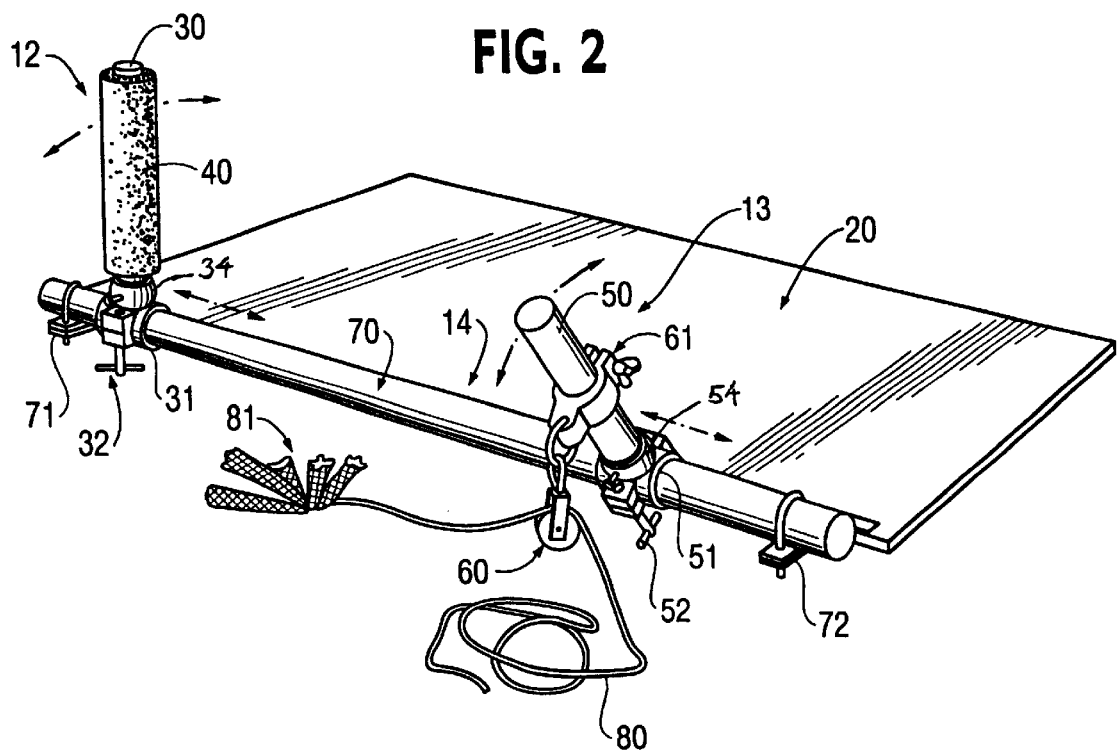
FIG. 2 is an isolated perspective view of the first version of the preferred embodiment.
Figure 3:
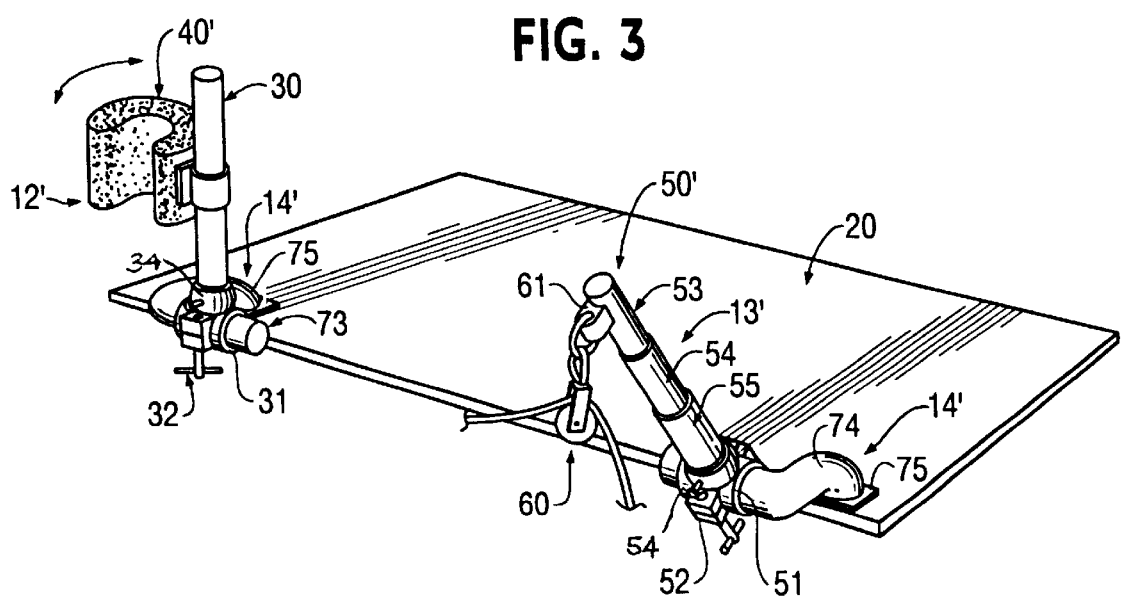
FIG. 3 is an isolated perspective view of the second version of the preferred embodiment of the invention.

As shown in FIGS. 1 through 3 in both versions of the preferred embodiment, the main support unit (11) comprises in general an elongated flat rectangular base platform member (20) dimensioned to underlie a substantial portion of a patient's torso (100) and rest upon the top of a medical examination table (200) or the like; wherein, the weight of the patient's body will immobilize the base platform member (20) relative to the examination table (200) or the like in a well recognized fashion.

In the first version of the preferred embodiment depicted in FIGS. 1 and 2, it can be seen that the limb immobilizing unit (12) comprises in general: a first elongated one-piece support post member (30) operatively associated with base platform members (20) in a manner that will be described in greater detail further on in the specification; and, a generally hollow cylindrical padded member (40) disposed in a surrounding relationship relative to the support post member (30).

In addition, the bottom portion of the support post member (30) is further provided with a hollow, generally cylindrical split ring coupling element (31) having an adjustment/locking mechanism (32) that can expand and contract the inside diameter of the split ring coupling element (31) and a universal swivel joint (34) whose purpose and function will be explained in greater detail further on in the specification.

Still referring to FIGS. 1 and 2, it can be seen that the pulley unit (13) comprises a second elongated support post member (50) whose lower position is likewise provided with a hollow, generally cylindrical split ring coupling element (51) having an adjustable/locking mechanism (52) that can expand and contract the inside diameter of the coupling element (51) and a universal swivel joint (54) for the reasons that will be explained presently.

In addition, the pulley unit (13) also includes a pulley member (60) that is suspended from the second support post member (50) by an adjustable clamp element (61) that is slidably disposed on the second support post member (50) for varying the position of the pulley member (60) relative to the second support post member (50).

Furthermore, as can best be appreciated by reference to FIG. 2, the rail unit (14) in the first version of the preferred embodiment comprises an elongated rail member (70) disposed in a raised, cantilevered fashion relative to the base platform member (20) by a pair of mounting brackets (71) (72) attached at spaced locations along one edge of the base platform member (20) of the first and second support post members (30) and (50) respectively and captively engaged at selected locations by the adjustment/locking mechanisms (32) (52) such that the arm immobilizing unit (12) and the pulley unit (13) can be disposed at selected locations along the elongated rail member (70) and angularly adjusted by rotating the split ring coupling elements (31) and (51) relative to their respective universal joints (34) and (54) to a desired angular orientation prior to employing the adjustment/locking mechanism (32) (52) to captively engage the arm immobilizing unit (12) and the pulley unit (13) relative to the rail unit.

It should also be noted at this juncture that the height of the pulley member (60) relative to the base platform member (20) can be varied by moving the adjustable clamp element (61) up and down on the second support post member (50); wherein, the pulley member (60) is adapted to receive an elongated tether (80) having one end provided with a plurality of finger traps (81) that will captively engage a patient's fingers to provide traction on the patient's arm when a conventional traction weight (not shown) is suspended from the other end of the elongated tether (80) in a well recognized fashion.

Turning now to FIGS. 3 through 6, it can be seen that while both the first and second versions of the preferred embodiment of the invention contain a certain number of identical structural components which are identified by the same reference numeral, there is also a number of structural distinctions between the two versions which will now be described in detail.

Figure 5:
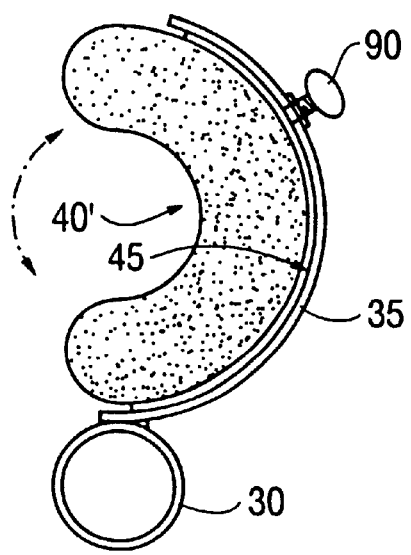
FIG. 5 is a top plan view of the arm immobilizing unit in the retracted mode.
Figure 6:
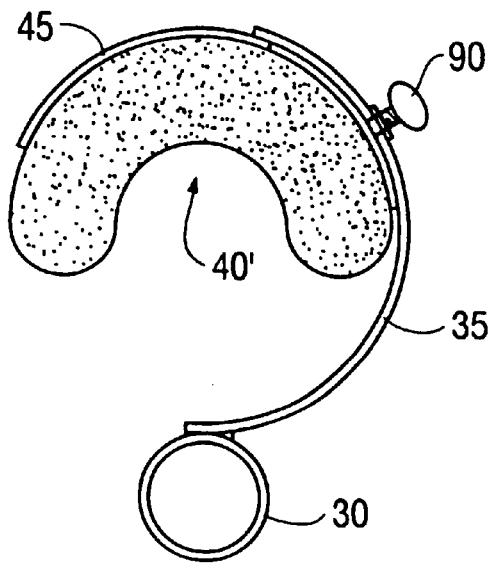
FIG. 6 is a top plan view of the arm immobilizing unit in the fully extended mode.

First of all, as can be seen by reference to FIGS. 3, 5, and 6, in the second version of the preferred embodiment while the arm immobilizing unit (12') also includes a first elongated support post member (30) having a generally hollow cylindrical split ring coupling element (31) provided with an adjustment/locking mechanism (32) and a universal swivel joint (34), the padded member (40') has a generally semi-cylindrical configuration and is mounted in an offset movable relationship relative to the first support post member (30).

In addition, both the first support post member (30) and the padded member (40') are provided with generally C-shaped bracket elements (35) and (45) respectively; wherein, the bracket elements (35) and (45) are slidably engagable with one another and provided with a locking mechanism (90) for captively engaging the padded member (40') in either an anterior or a superior position relative to a patient's upraised arm.

Figure 4:
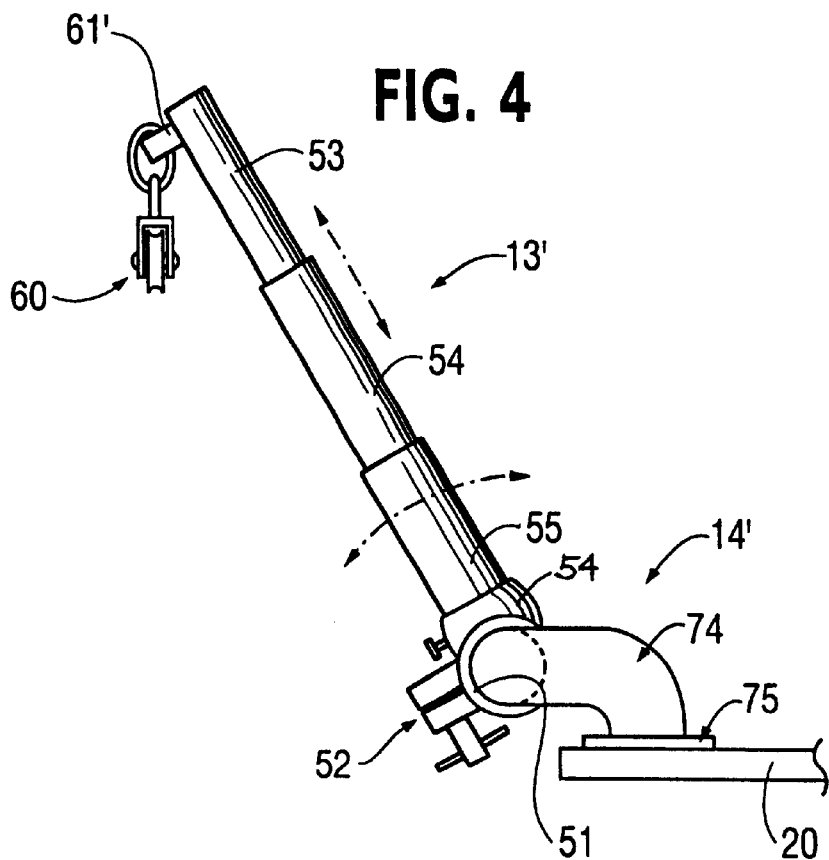
FIG. 4 is a side elevation view of the adjustable angle telescoping pulley unit.

Turning now to FIGS. 3 and 4, it can be seen that the pulley unit (13') of the second version of the preferred embodiment is also provided with a second support post member (50'). However, in this version, the second support post member (50') comprises a plurality of telescoping support post sections (53) (54) (55); wherein, the lower telescoping support post section (55) is provided with a generally hollow cylindrical split ring coupling element (51) having an adjustment/locking mechanism (52) and a universal swivel joint (54); and, wherein the upper telescoping support post section (53) is provided with a fixed bracket (61') for suspending the pulley member (60) at a desired height above the base platform member (20).

As can also be seen by reference to FIGS. 3 and 4, the rail unit (14') in the second version of the preferred embodiment comprises a pair of generally short contoured rail segments (74) (75) whose outboard ends are attached at widely spaced locations proximate one edge of the base platform member (20).

In this particular version, the rail segments (74) (75) are widely spaced relative to one another so as to permit for unobstructed radiographic imaging of a patient's limb.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An angularly adjustable traction apparatus for applying traction forces to a limb of a patient wherein the apparatus comprises:

a support unit including an elongated base platform member dimensioned to underlie a portion of a patient's torso;

a rail unit including an elongated one-piece rail member having a length cord disposed in a raised fashion relative to one edge of the base platform member;

a limb immobilizing unit including a first elongated support post member having a lower portion movably connected to said rail member;

a pulley unit including a second elongated support post member having a lower portion movably connected to said rail member and an upper portion and a pulley member associated with the upper portion of the second elongated support post member; and, first means associated with the lower portions of both the first and second elongated support post members for independently varying the angular orientation of both the first and second support post members in a vertical plane perpendicular to said rail member and providing translational movement along the length of said rail member.

2. The apparatus as in claim 1, further comprising:

second means for adjusting the height of the pulley member relative to the base platform member.

3. The apparatus as in claim 2, said first means further proving laterally spacing said first and second elongated support post members along said rail member.

4. The apparatus as in claim 1, wherein, said first means comprises a pair of split ring coupling elements dimensioned to be slidably received on the elongated rail member; wherein, each of the split ring coupling elements is associated with the lower portion of one of the first and second support post members and further provided with an adjustment/locking mechanism and a universal swivel joint.

5. The apparatus as in claim 4, wherein, both the first and second support post members comprise one-piece support post members.

6. The apparatus as in claim 5, wherein, the first support post member is further provided with a hollow cylindrical padded member.

7. The apparatus as in claim 6, wherein, the pulley member is further provided with an adjustable clamp element that is adapted to be movably connected to the upper portion of the second support post member.

* * * * *